(12) United States Patent
Ishige et al.

(10) Patent No.: US 7,863,438 B2
(45) Date of Patent: Jan. 4, 2011

(54) STABLE SALT OF 3'-PHOSPHOADENOSINE 5'-PHOSPHOSULFATE

(75) Inventors: Kazuya Ishige, Choshi (JP); Takashi Kawakami, Yokosuka (JP); Toshitada Noguchi, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 377 days.

(21) Appl. No.: 12/093,743

(22) PCT Filed: Nov. 16, 2006

(86) PCT No.: PCT/JP2006/322893

§ 371 (c)(1),
(2), (4) Date: Jul. 9, 2008

(87) PCT Pub. No.: WO2007/058278

PCT Pub. Date: May 24, 2007

(65) Prior Publication Data

US 2009/0118491 A1 May 7, 2009

(30) Foreign Application Priority Data

Nov. 17, 2005 (JP) .............................. 2005-333047

(51) Int. Cl.
*C07H 19/22* (2006.01)
(52) U.S. Cl. .................. 536/27.13; 536/25.3; 536/27.1; 536/27.11
(58) Field of Classification Search ........................ None
See application file for complete search history.

(56) References Cited

FOREIGN PATENT DOCUMENTS

| GB | 1017149 | 1/1966 |
|---|---|---|
| JP | 4 178328 | 6/1992 |
| JP | 5 137588 | 6/1993 |
| JP | 2002 249497 | 9/2002 |
| JP | 2003 55395 | 2/2003 |

*Primary Examiner*—Patrick T Lewis
(74) *Attorney, Agent, or Firm*—Oblon, Spivak, McClelland, Maier & Neustadt, L.L.P.

(57) ABSTRACT

The present invention provides a stable salt of 3'-phosphoadenosine 5'-phosphosulfate (PAPS) and a production method therefor.

The present invention is directed to a stable salt of PAPS (amine salt), which is formed between PAPS and an amine compound, and to a method for producing a stable salt of PAPS, which includes adding an amine compound to an aqueous PAPS solution in an amount by mole equal to or greater than that of PAPS, and lyophilizing the resultant solution.

The present invention has first realized production of a solid-form PAPS salt having considerably improved stability through a very simple technique. Since the thus-produced amine salt of PAPS is very stable, the salt can be stored or employed without taking much care about decomposition thereof at ambient temperature.

15 Claims, No Drawings

STABLE SALT OF 3'-PHOSPHOADENOSINE 5'-PHOSPHOSULFATE

TECHNICAL FIELD

The present invention relates to a stable salt of 3'-phosphoadenosine 5'-phosphosulfate (PAPS), which is considerably unstable in solid form.

BACKGROUND ART

PAPS serves as a sulfate donor which is present in a wide range of living organisms, including microorganisms, plants, and higher animals. PAPS has been reported to be related to several diseases (e.g., proteoglycan-associated diseases). Thus, efforts will be made to realize use of PAPS as pharmaceutical products or health foods in the future.

There have been conventionally reported various methods for synthesizing PAPS (e.g., a chemical synthesis method and an enzymatic synthesis method), in which a lithium salt or sodium salt of PAPS is produced in the form of powder (see, for example, Non-Patent Document 1 and Patent Document 1).

Non-Patent Document 1: Merck Calbiochem Catalog (2005/06), page 32

Patent Document 1: JP-A-1993-137588

DISCLOSURE OF THE INVENTION

Problems to be Solved by the Invention

However, as shown in the description "Note: unstable at room temperature" in the aforementioned catalog, or in the Referential Example described hereinbelow, a solid PAPS metal salt (lithium salt or sodium salt) per se is considerably unstable, and is readily decomposed at ambient temperature. Thus, highly pure PAPS is very difficult to isolate and to maintain or store in a stable state. This is a major obstacle to realize industrial application of PAPS.

Therefore, in view that overcoming instability of solid-form PAPS is required for realizing industrial application of PAPS, an object of the present invention is to provide a stable salt of PAPS.

Means for Solving the Problems

The present inventors have conducted extensive studies for overcoming instability of solid-form PAPS, and as a result have found that a salt prepared from PAPS and an amine compound has excellent stability. The present invention has been accomplished on the basis of this finding. Accordingly, the present invention provides the following.

(1) A stable salt of PAPS, which is formed between PAPS and an amine compound.

(2) A stable salt as described in (1) above, wherein the amine compound is a compound having one or more amino groups or imino groups.

(3) A stable salt as described in (1) above, wherein the amine compound is a secondary amine.

(4) A stable salt as described in (1) above, wherein the amine compound is a secondary amine having a C1-C10 hydrocarbon chain.

(5) A stable salt as described in (1) above, wherein the amine compound is diethylamine or piperidine.

(6) A stable salt as described in (1) above, wherein the amine compound is a tertiary amine.

(7) A stable salt as described in (1) above, wherein the amine compound is a tertiary amine having a C1-C7 hydrocarbon chain.

(8) A stable salt as described in (1) above, wherein the amine compound is trimethylamine, triethylamine, or triethanolamine.

(9) A stable salt as described in (1) above, wherein the amine compound is a polyamine.

(10) A stable salt as described in (1) above, wherein the amine compound is putrescine or polyethyleneimine.

(11) A stable salt as described in (1) above, wherein the amine compound is an amino acid.

(12) A stable salt as described in (1) above, wherein the amine compound is L-histidine.

(13) A method for producing a stable salt of PAPS, comprising adding an amine compound to an aqueous PAPS solution in an amount by mole equal to or greater than that of PAPS; and lyophilizing the resultant solution.

(14) A method for producing a stable salt of PAPS as described in (13) above, wherein the amine compound or an aqueous solution thereof is added so as to attain a pH of 5 or higher.

(15) A method for producing a stable salt of PAPS as described in (13) above, wherein the amine compound or an aqueous solution thereof is added so as to attain a pH of 5 to 10.

EFFECTS OF THE INVENTION

The present invention has first realized production of a solid-form PAPS salt having considerably improved stability through a very simple technique. Since the thus-produced amine salt of PAPS is very stable, the salt can be stored or employed with no worry about decomposition thereof at ambient temperature.

BEST MODES FOR CARRYING OUT THE INVENTION

As used herein, the term "stable salt" of PAPS refers to a PAPS salt which, when weighed (10 mg) and allowed to stand still in a desiccator (relative humidity: 20% or less) at ambient temperature (23±2° C.) for seven days, exhibits a percent undecomposed of 80% or more (preferably 90% or more) as measured through quantitative determination of the PAPS content by HPLC. Salts exhibiting a percent undecomposed of less than 80% do not fall within the definition of the stable salt of the present invention. HPLC conditions are as follows.

<HPLC Conditions>
  Separation column: ODS-A312 column (product of YMC)
  Eluent: 50 mM Aqueous potassium dihydrogenphosphate solution
  Flow rate: 0.6 mL/minute
  Detection: Absorbance (A) at 270 nm
  Temperature: 20° C.

As described above, the present invention relates to a stable salt (amine salt) of PAPS formed between PAPS and an amine compound.

No particular limitation is imposed on the amine compound employed for preparing a stable salt of PAPS, so long as the compound has one or more amino groups or imino groups, and the resultant salt falls within the aforementioned scope of the stable salt.

Examples of the amine compound include a secondary amine, a tertiary amine, a polyamine, and an amino acid.

The secondary amine preferably has a C1-C10 hydrocarbon chain. Specific examples of such a secondary amine include dimethylamine, diethylamine, dipropylamine, diisopropylamine, dibutylamine, diamylamine, diallylamine, diphenylamine, and piperidine. Particularly preferred are diethylamine and piperidine.

The tertiary amine preferably has a C1-C7 hydrocarbon chain. Specific examples of such a tertiary amine include trimethylamine, triethylamine, tripropylamine, tributylamine, triamylamine, triallylamine, triphenylamine, and triethanolamine. Particularly preferred are triethylamine and triethanolamine.

Examples of the polyamine include biogenic polyamines (e.g., diamines, triamines, and tetramines); and a polymer compound having, in a side chain or main chain thereof, an amino group or an imino group. Specific examples of biogenic polyamines include putrescine, spermine, and spermidine; and specific examples of the polymer compound include polyethyleneimine, polyallylamine, and polyvinylamine. Particularly preferred is polyethyleneimine.

Examples of the amino acid include basic amino acids. Particularly preferred is L-histidine.

Such a stable salt of PAPS may be prepared by adding an amine compound to an aqueous PAPS solution in an amount by mole equal to or greater than that of PAPS, and by lyophilizing the resultant solution.

Specifically, a stable salt of PAPS in a solid form (e.g., white powder) may be produced through the following procedure: an aqueous PAPS solution is prepared through a known chemical synthesis or enzymatic synthesis method (the solution is employed as is, or optionally purified); an amine compound or an aqueous solution thereof is added to the PAPS solution such that the amount by mole of the amine compound is equal to or greater than that of PAPS, so as to attain a pH of 5 or higher (preferably a pH of 5 to 10); and the resultant product is lyophilized through a customary method.

The thus-produced stable salt of PAPS exhibits a stability considerably higher than that of a conventional PAPS metal salt. Despite exhibiting such a high stability, the stable salt is preferably stored in a hermetically sealed container at a low temperature of 4° C. or lower, from the viewpoint of ensuring stability.

EXAMPLES

The present invention will next be specifically described in detail with reference to Referential Example and Example. However, it will be understood that the present invention is not limited to the Example. Quantitative determination of PAPS was performed under the aforementioned HPLC conditions.

Referential Example

Ambient-Temperature Stability of PAPS Lithium Salt in Aqueous Solution or in the Form of Powder Ambient-temperature stability of a PAPS lithium salt (product of Calbiochem) was evaluated in an aqueous solution or in the form of powder as follows. Specifically, an aqueous PAPS lithium salt solution (concentration: 10 mg/mL) was prepared, and the solution was allowed to stand still at 4° C. or ambient temperature (23° C.). In parallel therewith, the PAPS lithium salt was weighed (10 mg), and allowed to stand still as is (i.e., in the form of powder) at 4° C. or ambient temperature (23° C.). The percentage of undecomposed PAPS was measured after the aqueous solution or the powder had been allowed to stand still for seven days. The results are shown in Table 1. As used herein, "percent undecomposed" or "percentage of undecomposed PAPS" is the ratio of the remaining amount of PAPS to the initial amount thereof. As is clear from data shown in Table 1, the commercially available PAPS lithium salt is relatively stable in an aqueous solution, but is very unstable in the form of powder (i.e., decomposed by 35% after being allowed to stand still at ambient temperature for seven days).

TABLE 1

| Form of still standing | Undecomposed of PAPS (%) | |
|---|---|---|
| | 4° C. | 23° C. |
| Aqueous solution | >99 | 96 |
| Powder | 89 | 65 |

Example 1

(1) Preparation of PAPS Salts (Powders)

PAPS lithium salt (product of Calbiochem) was caused to pass through a column charged with a cation exchange resin DIAION® PK-216 (product of Mitsubishi Chemical Corporation), to thereby yield an aqueous solution of PAPS of free acid form. Immediately thereafter, the aqueous solution was neutralized with an aqueous solution of lithium hydroxide, sodium hydroxide, potassium hydroxide, aqueous ammonia, L-lysine, L-arginine, L-histidine, piperidine, ethylamine, ethanolamine, diethylamine, trimethylamine, triethylamine, triethanolamine, putrescine, or polyethyleneimine, so as to attain a pH of 7.0, thereby preparing a solution of a corresponding salt (i.e., lithium salt, sodium salt, potassium salt, ammonium salt, L-lysine salt, L-arginine salt, L-histidine salt, piperidine salt, ethylamine salt, ethanolamine salt, diethylamine salt, trimethylamine salt, triethylamine salt, triethanolamine salt, putrescine salt, or polyethyleneimine salt) of PAPS. The resultant solution was lyophilized, to thereby yield a powdery PAPS salt.

(2) Stability of Powdery PAPS Salt at Ambient Temperature

Each of the powdery PAPS salts prepared in Example 1 was weighed (10 mg), and allowed to stand still in a desiccator (relative humidity: 10%) at ambient temperature (23±2° C.) for seven days. Thereafter, the percentage of undecomposed PAPS was measured through HPLC. The results are shown in Table 2.

As shown in Table 2, a metal salt (e.g., sodium salt, lithium salt, or potassium salt) of PAPS exhibited low stability; i.e., such a metal salt exhibited a percentage of undecomposed PAPS of 65% or less after being allowed to stand still for seven days at ambient temperature. An ammonium salt, primary amine salt (i.e., ethylamine salt, ethanolamine salt), L-lysine salt, or L-arginine salt of PAPS exhibited a stability lower than that of the aforementioned metal salt.

In contrast, a diethylamine salt or piperidine salt (i.e., secondary amine salt), a trimethylamine salt, triethylamine salt, or triethanolamine salt (i.e., tertiary amine salt), a putrescine salt or polyethyleneimine salt (i.e., polyamine salt), or an L-histidine salt (i.e., amino acid salt) of PAPS was remarkably stabilized, and any of these PAPS salts exhibited a percentage of undecomposed PAPS of 80% or more after being allowed to stand still for seven days at ambient temperature. As is clear from data shown in Table 2, among these PAPS salts, particularly preferred salt forms are the diethylamine salt, the piperidine salt, the triethylamine salt, the triethanolamine salt, the polyethyleneimine salt, and the L-histidine salt, which exhibited a percentage of undecomposed PAPS of 90% or more.

TABLE 2

|  |  | Undecomposed PAPS (%) |
|---|---|---|
| PAPS salts | | |
| Secondary amine | Diethylamine salt | 96 |
|  | Piperidine salt | 92 |
| Tertiary amine | Triethylamine salt | 100 |
|  | Triethanolamine salt | 95 |
|  | Trimethylamine salt | 89 |
| Polyamine | Polyethyleneimine salt | 94 |
|  | Putrescine salt | 80 |
| Amino acid | L-Histidine salt | 98 |
| Referential salts | | |
| Sodium salt | | 64 |
| Lithium salt | | 65 |
| Potassium salt | | 22 |
| Ammonium salt | | 4.1 |
| Imidazole salt | | 2.9 |
| Ethylamine salt | | 48 |
| Ethanolamine salt | | 13 |
| L-Lysine salt | | 27 |
| L-Arginine salt | | 57 |

The invention claimed is:

1. A stable salt of PAPS, which is formed between PAPS, which is 3'-phosphoadenosine 5'-phosphosulfate, and an amine compound.

2. A stable salt according to claim 1, wherein the amine compound is a compound having one or more amino groups or imino groups.

3. A stable salt according to claim 1, wherein the amine compound is a secondary amine.

4. A stable salt as according to claim 1, wherein the amine compound is a secondary amine having a C1-C10 hydrocarbon chain.

5. A stable salt according to claim 1, wherein the amine compound is diethylamine or piperidine.

6. A stable salt according to claim 1, wherein the amine compound is a tertiary amine.

7. A stable salt according to claim 1, wherein the amine compound is a tertiary amine having a C1-C7 hydrocarbon chain.

8. A stable salt according to claim 1, wherein the amine compound is trimethylamine, triethylamine, or triethanolamine.

9. A stable salt according to claim 1, wherein the amine compound is a polyamine.

10. A stable salt according to claim 1, wherein the amine compound is putrescine or polyethyleneimine.

11. A stable salt according to claim 1, wherein the amine compound is an amino acid.

12. A stable salt according to claim 1, wherein the amine compound is L-histidine.

13. A method for producing a stable salt of PAPS, comprising adding an amine compound to an aqueous PAPS solution in an amount by mole equal to or greater than that of PAPS, and lyophilizing the resultant solution.

14. A method for producing a stable salt of PAPS according to claim 13, wherein the amine compound or an aqueous solution thereof is added so as to attain a pH of 5 or higher.

15. A method for producing a stable salt of PAPS according to claim 13, wherein the amine compound or an aqueous solution thereof is added so as to attain a pH of 5 to 10.

* * * * *